United States Patent [19]

Regel et al.

[11] 4,246,274

[45] Jan. 20, 1981

[54] ANTIMYCOTIC HYDROXYPROPYL-IMIDAZOLES

[75] Inventors: Erik Regel; Karl H. Büchel; Ingo Haller; Manfred Plempel, all of Wuppertal, Fed. Rep. of Germany

[73] Assignee: Bayer Aktiengesellschaft, Leverkusen, Fed. Rep. of Germany

[21] Appl. No.: 30,799

[22] Filed: Apr. 17, 1979

[30] Foreign Application Priority Data

May 10, 1978 [DE] Fed. Rep. of Germany ....... 2820489
Jul. 26, 1978 [DE] Fed. Rep. of Germany ....... 2832677

[51] Int. Cl.$^3$ .................. A61K 31/415; C07D 233/60
[52] U.S. Cl. .................................. 424/273 R; 548/341
[58] Field of Search ..................... 548/341; 424/273 R

[56] References Cited

U.S. PATENT DOCUMENTS

| | | | |
|---|---|---|---|
| 3,940,414 | 2/1976 | Krämer et al. | 548/341 |
| 3,940,415 | 2/1976 | Büchel et al. | 424/273 R |
| 4,052,409 | 10/1977 | Büchel et al. | 548/341 |
| 4,101,665 | 7/1978 | Heeres | 548/341 |

FOREIGN PATENT DOCUMENTS

| | | | |
|---|---|---|---|
| 2623129 | 5/1976 | Fed. Rep. of Germany | 548/341 |
| 2705676 | 8/1978 | Fed. Rep. of Germany | 548/341 |

*Primary Examiner*—Henry R. Jiles
*Assistant Examiner*—Richard A. Schwartz
*Attorney, Agent, or Firm*—Sprung, Felfe, Horn, Lynch & Kramer

[57] ABSTRACT

The invention includes as a series of 2-(substituted-phenyl)-1-aryl-3-(imidazol-1-yl)-propan-2-ols useful as antimicrobial agents. Also included in the invention are methods for the manufacture of the above-identified imidazol-1-yl-propan-2-ols, compositions containing said compounds and the use of said compounds and compositions for antimicrobial use.

11 Claims, No Drawings

ANTIMYCOTIC HYDROXYPROPYL-IMIDAZOLES

The present invention relates to certain new hydroxypropyl-imidazole compounds, to processes for their preparation and to their use as antimycotics.

It has already been disclosed that 1-(β-aryl)-ethylimidazole derivatives, such as, in particular, 1-[2,4-di-chloro-β-(2,4-dichlorobenzyloxy)-phenethyl]-imidazole nitrate ("Miconazol" (Trade Mark)), display a good antimycotic action (compare DE-AS (German Published Specification) No. 1,940,388). However, their action in vivo, such as, in particular, against Candida, is not always satisfactory.

According to the present invention we provide compounds which are hydroxypropyl-imidazoles of the general formula

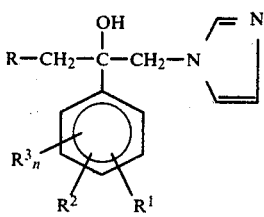

or a salt thereof,
in which
R denotes an optionally substituted phenyl, naphthyl or 1,2,3,4-tetrahydronaphthyl radical,
$R^1$ denotes an optionally substituted phenyl or cycloalkyl radical and
$R^2$ denotes a hydrogen atom, or
$R^1$ and $R^2$ together, in the o-position relative to each other, denote an optionally substituted, multi-membered methylene bridge or, together with the phenyl ring, denote a naphthyl radical,
$R^3$ denotes a halogen atom, or an alkyl, alkoxy or halogenoalkyl group, each of said alkyl, alkoxy and halogenoalkyl groups having up to 4, preferably up to 2 carbon atoms and
n is 0, 1, 2 or 3, The compounds of the invention display powerful antimycotic properties.

The compounds of the invention may be prepared by reacting (a) an imidazolyl-methyl phenyl ketone of the general formula

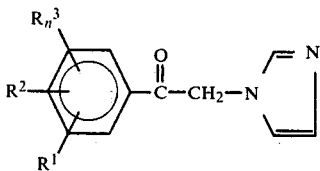

in which
$R^1$, $R^2$, $R^3$ and n have the meaning indicated above, with a Grignard compound of the general formula

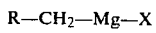

R—CH₂—Mg—X (III)

in which
R has the meaning indicated above and

X denotes a halogen atom, preferably a chlorine or bromine atom,
in the presence of a diluent, or (b) a 1-halogeno-propan-2-ol of the general formula

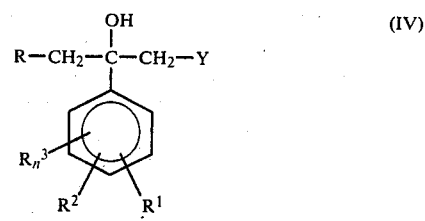

in which
R, $R^1$, $R^2$, $R^3$ and n have the meaning indicated above and
Y denotes a halogen atom, preferably a chlorine or bromine atom,
with imidazole, preferably in the presence of an acid-binding agent and preferably in the presence of a diluent. In some cases, it proves advantageous to employ an alkali metal salt of imidazole, such as the sodium salt or potassium salt, instead of imidazole.

The hydroxypropyl-imidazoles obtainable according to the invention can be converted into salts by reaction with acids.

Surprisingly, in addition to a good antimycotic in vitro activity, the hydroxypropyl-imidazoles according to the invention exhibit a better, therapeutically usable in vivo activity against Candida than 1-[2,4-dichloro-β-(2,4-dichlorobenzyloxy)-phenethyl]-imidazole nitrate, which is known from the state of the art and is acknowledged as a good agent of the same type of action.

Preferred hydroxypropyl-imidazoles of the formula (I) according to the invention are those in which R represents optionally substituted phenyl, naphthyl or 1,2,3,4-tetrahydronaphthyl, preferred possible substituents which may be mentioned being: halogen, in particular fluorine, chlorine and bromine, straight-chain or branched alkyl and alkoxy with in each case 1 to 4 carbon atoms, and halogenoalkyl with 1 to 4 carbon atoms and up to 5 halogen atoms, in particular with 1 or 2 carbon atoms and up to 3 identical or different halogen atoms, halogen atoms being, in particular, fluorine and chlorine and trifluoromethyl being mentioned as an example; $R^1$ represents optionally substituted phenyl or cycloalkyl with 3 to 7 carbon atoms, preferred possible substituents which may be mentioned being: halogen, in particular fluorine, chlorine or bromine, alkyl with 1 to 4, in particular 1 to 3, carbon atoms, and alkenyl with 2-4 carbon atoms, and $R^2$ represents hydrogen, or $R^1$ and $R^2$ together, in the ortho-position relative to one another, represent a methylene bridge which as 3 to 5 methylene groups and is optionally monosubstituted or polysubstituted, preferred possible substitutents which may be mentioned being: halogen, in particular fluorine, chlorine or bromine, and alkyl with 1 to 4, in particular with 1 to 2, carbon atoms; or $R^1$ and $R^2$, together with the phenyl ring, represent naphthyl; $R^3$ represents halogen, in particular fluorine, chlorine and bromine, straight-chain or branched alkyl and alkoxy with in each case 1 to 4 carbon atoms, and halogenoalkyl with 1 to 4 carbon atoms and up to 5 halogen atoms, in particular with 1 or 2 carbon atoms and up to 3 identical or different halogen atoms, halogen atoms being, in particular, fluorine and chlorine and trifluoromethyl being mentioned as an example; and the index n represents the number 0, 1 or 2.

Compounds of the formula (I) which are very particularly preferred are those in which R represents phenyl which is optionally monosubstituted or disubstituted by chlorine, fluorine or methyl, or naphthyl or 1,2,3,4-tetrahydronaphthyl; $R^1$ represents phenyl, cyclopentyl or cyclohexyl, which are optionally monosubstituted or disubstituted by chlorine, bromine, fluorine, methyl, ethyl, isopropyl or isopropenyl, and $R^2$ represents hydrogen, or $R^1$ and $R^2$ together, in the ortho-position relative to one another, represent a trimethylene, tetramethylene or pentamethylene bridge which is optionally substituted by chlorine or methyl, or, together with the phenyl ring, represent naphthyl; $R^3$ represents chlorine, fluorine or methyl and n is 0 or 1.

If, for example, 4-biphenylyl imidazol-1-yl-methyl ketone and 4-chlorobenzyl-magnesium chloride are used as starting substances, the course of the reaction can be represented by the equation which follows (process (a)):

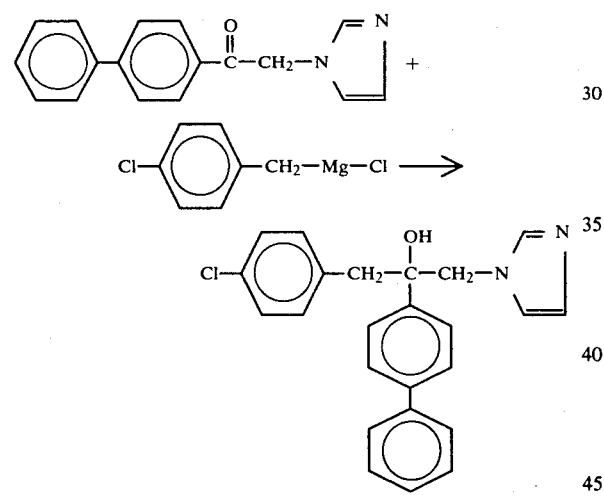

If 2-(4-biphenylyl)-3-chloro-1-(2,4-dichlorophenyl)-propan-2-ol and sodium imidazole are used as starting substances, the course of the reaction can be represented by the equation which follows (process (b)):

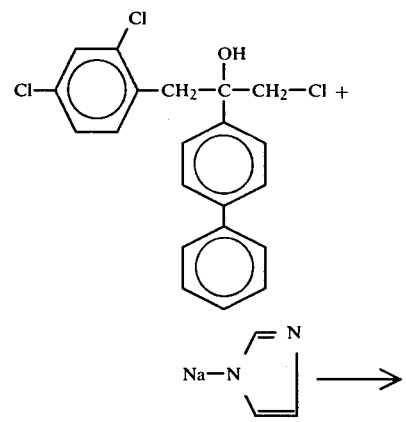

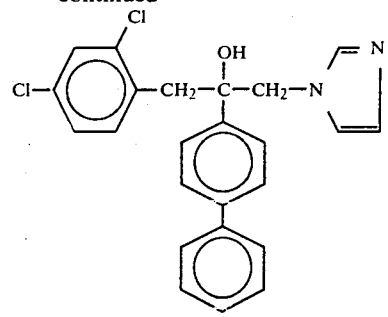

The formula (II) provides a general definition of the imidazolylmethyl phenyl ketones to be used as starting substances for process variant (a). In this formula, $R^1$, $R^2$ and $R^3{}_n$ preferably represent the radicals which have already been mentioned as preferred in the case of the compounds of the formula (I).

The imidazolylmethyl phenyl ketones of the formula (II) are not yet known. However, they can be prepared in a generally customary and known manner by reacting corresponding phenacyl halides of the formula

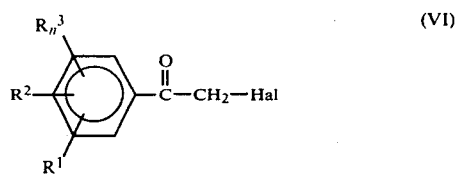

in which $R^1$, $R^2$, $R^3$ and n have the meaning indicated above and

Hal represents chlorine or bromine, with imidazole in the presence of a diluent, such as, for example, dimethylformamide, and in the presence of an acid-binding agent, such as, in particular, an excess of imidazole, at temperatures between 20° and 80° C. (in this context, compare also the statements in U.S. Pat. No. 3,658,813 and the preparation examples).

Examples which may be mentioned of the starting substances of the formula (II) are: 4-biphenylyl imidazol-1-yl-methyl ketone, 4-(4'-chlorobiphenylyl-)imidazol-1-yl-methyl ketone, 2-biphenylyl imidazol-1-yl-methyl ketone, 4-(2',4'-dichlorobiphenylyl) imidazol-1-yl-methyl ketone, 2-chloro-4-biphenylyl imidazol-1-yl-methyl ketone, 2-chloro-4-(4'-chlorobiphenylyl) imidazol-1-yl-methyl ketone, 4-cyclohexylphenyl imidazol-1-yl-methyl ketone, 4-cyclopentylphenyl imidazol-1-yl-methyl ketone, 4-chloro-3-cyclohexylphenyl imidazol-1-yl-methyl ketone, 4-(3-bromocyclohexyl)-phenyl imidazol-1-yl-methyl ketone, 4-cyclopentyl-2-chlorophenyl imidazol-1-yl-methyl ketone, 4-cyclopentyl-2-fluorophenyl imidazol-1-yl-methyl ketone, 4-cyclopentyl-2-methylphenyl imidazol-1-yl-methyl ketone, 4-(1-methylcyclohexyl)-phenyl imidazol-1-yl-methyl ketone, 4-cycloheptylphenyl imidazol-1-yl-methyl ketone, 4-cycloheptyl-2-chlorophenyl imidazol-1-yl-methyl ketone, naphth-1-yl imidazol-1-yl-methyl ketone, naphth-2-yl imidazol-1-yl-methyl ketone, 1,2,3,4-tetrahydronaphth-5-yl imidazol-1-yl-methyl ketone, 1,2,3,4-tetrahydronaphth-6-yl imidazol-1-yl-methyl ketone and indan-4-yl imidazol-1-yl-methyl ketone.

The formula (III) provides a general definition of the Grignard compounds also to be used as starting substances for process variant (a). In this formula, R preferably represents the radicals which have already been mentioned as preferred in the case of the compounds of the formula (I).

The Grignard compounds of the formula (III) are generally known compounds of organic chemistry. Examples which may be mentioned are: benzyl-magnesium chloride, 4-chlorobenzyl-magnesium chloride, 2,4-dichlorobenzyl-magnesium chloride, 2,6-dichlorobenzyl-magnesium chloride, 2-chloro-6-fluorobenzyl-magnesium chloride, 2-chlorobenzyl-magnesium chloride, 3-chlorobenzyl-magnesium chloride, 3,4-dichlorobenzyl-magnesium chloride, naphth-2-2-methyl-magnesium chloride, 1,2,3,4-tetrahydronaphth-6-yl-methyl-magnesium chloride and the corresponding bromides.

The formula (IV) provides a general definition of the 1-halogeno-propan-2-ols to be used as starting substances for process variant (b). In this formula, R, $R^1$, $R^2$ and $R^3_n$ preferably represent the radicals which have already been mentioned as preferred in the case of the compounds of the formula (I).

The 1-halogeno-propan-2-ols of the formula (IV) are not yet known. However, they can be prepared in a generally customary and known manner, by reacting ketones of the formula (IV) with Grignard compounds of the formula (III) in a manner corresponding to process variant (a) (in this context, compare also the statements of DE-OS (German Published Specification) No. 2,623,129 and the preparation examples).

Possible diluents for the reaction, according to the invention, in process (a) are all the solvents customary for a Grignard reaction. These include, preferably, ethers, such as diethyl ether or tetrahydrofurane and mixtures with other organic solvents, such as, for example, benzene.

The reaction temperatures can be varied within a substantial range in process (a). In general, the reaction is carried out between about 20° and about 120° C., preferably between about 30° and about 80° C.

In carrying out process (a), an excess of 3 to 5 mols of the Grignard compound of the formula (III) is preferably employed per 1 mol of the compound of the formula (II). Isolation of the compounds of the formula (I) is effected in a customary and known manner.

Preferred possible diluents for the reaction, according to the invention, in process (b) are inert organic solvents. These include, preferably, ketones, such as diethyl ketone, and in particular acetone and methyl ethyl ketone; nitriles, such as propionitrile, and in particular acetonitrile; alcohols, such as ethanol or isopropanol; ethers, such as tetrahydrofurane or dioxane; aromatic hydrocarbons, such as benzene, toluene and dichlorobenzene; formamides, such as, in particular, dimethylformamide; and halogenated hydrocarbons, such as methylene chloride, carbon tetrachloride or chloroform.

If process (b) according to the invention is carried out in the presence of an acid-binding agent, it is possible to add any of the inorganic or organic acid-binding agents which can customarily be used, such as alkali metal carbonate or bicarbonate, e.g. sodium carbonate and potassium carbonate, and sodium bicarbonate, or such as lower tertiary alkylamines, cycloalkylamines or aralkylamines, for example triethylamine, N,N-dimethylcyclohexylamine, dicyclohexylmethylamine and N,N-dimethylbenzylamine, and furthermore pyridine and diazabicyclooctane. An excess of imidazole is preferably used.

The reaction temperatures can be varied within a substantial range in process (b). In general, the reaction is carried out between about 30° and 200° C., preferably at the boiling point of the solvent.

In carrying out process (b) according to the invention, 1 to 2.5 mols of imidazole and 1 to 2.5 mols of acid-binding agent are preferably employed per 1 mol of the compounds of the formula (IV). If an alkali metal salt is used, 1 to 1.5 mols of alkali metal salt are preferably employed per 1 mol of the compound of the formula (IV). In order to isolate the compounds of the formula (I), the solvent is distilled off and the residue is washed with water directly or after taking up in an organic solvent, and, if appropriate, the organic phase is dried over sodium sulphate and freed from solvent in vacuo. The residue is appropriately purified by distillation, recrystallisation or chromatography.

All the physiologically acceptable acids can be used for the preparation of acid addition salts of the compounds of the formula (I). These acids include, preferably, hydrogen halide acids, such as, for example, hydrochloric acid and hydrobromic acid, in particular hydrochloric acid, and furthermore phosphoric acid, nitric acid, sulphuric acid, monofunctional and bifunctional carboxylic acids and hydroxycarboxylic acids, such as, for example, acetic acid, maleic acid, succinic acid, fumaric acid, tartaric acid, citric acid, salicylic acid, sorbic acid and lactic acid, and sulphonic acids, such as, for example, p-toluenesulphonic acid and 1,5-naphthalenedisulphonic acid.

The salts of the compounds of the formula (I) can be obtained in a simple manner by customary salt formation methods, for example by dissolving a compound of the formula (I) in a suitable inert solvent and adding the acid, for example hydrochloric acid, and they can be isolated in a known manner, for example by filtration, and if appropriate purified by washing with an inert organic solvent.

Examples which may be mentioned of particularly active representatives of the active compounds according to the invention, in addition to the preparation examples and the examples in Table 1, are:

TABLE A

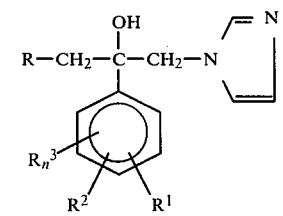

| Compound No. | R | $R^1$ | $R^2$ | $R^3_n$ |
|---|---|---|---|---|
| 1. | Cl—⌬ | 4—⌬ | H | — |
| 2. | Cl—⌬—Cl | 4—⌬ | H | — |
| 3. | ⌬⌬H | 4—⌬ | H | — |
| 4. | ⌬⌬ | 4—⌬ | H | — |

TABLE A-continued

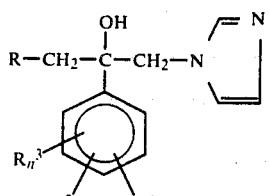

| Compound No. | R | R¹ | R² | $R_n^3$ |
|---|---|---|---|---|
| 5. | 3,4-diCl-phenyl | 4-phenyl | H | — |
| 6. | 3,4-diCl-phenyl | 4-Cl-phenyl | H | — |
| 7. | 3-Cl-phenyl | 3,4-(CH₂)₄— | | — |
| 8. | 3,4-diCl-phenyl | 3,4-(CH₂)₃— | | — |
| 9. | 3,4-diCl-phenyl | 4-phenyl | H | — |
| 10. | 4-F-phenyl | 4-Cl-phenyl | H | — |
| 11. | 4-F-phenyl | 4-F-phenyl | H | — |
| 12. | 4-F-phenyl | 4-phenyl | H | — |
| 13. | 2-F-phenyl | 4-phenyl | H | — |
| 14. | 2-F-phenyl | 4-CH₃-phenyl | H | — |
| 15. | 2-F-phenyl | 4-C₂H₅-phenyl | H | — |
| 16. | 2-F-phenyl | 4-isoC₃H₇-phenyl | H | — |
| 17. | 2-F-phenyl | 4-C(=CH₂)CH₃-phenyl | H | — |
| 18. | 2-Cl-phenyl | 4-phenyl | H | — |
| 19. | 2-Cl-phenyl | 4-CH₃-phenyl | H | — |
| 20. | 2-Cl-phenyl | 4-C₂H₅-phenyl | H | — |

TABLE A-continued

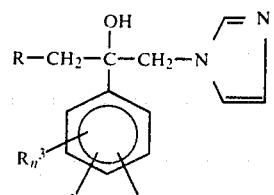

| Compound No. | R | R¹ | R² | $R_n^3$ |
|---|---|---|---|---|
| 21. | 2-Cl-phenyl | 4-isoC₃H₇-phenyl | H | — |
| 22. | 2-Cl-phenyl | 4-C(=CH₂)CH₃-phenyl | H | — |

The compounds of the formula (I) according to the invention, and their acid addition salts, display antimicrobial actions, in particular antimycotic actions. They possess a very broad antimycotic action spectrum, especially against dermatophytes and blastomyces as well as biphase fungi, for example against varieties of Candida, such as *Candida albicans,* varieties of Epidermophyton, such as *Epidermophyton floccosum,* varieties of Aspergillus, such as *Aspergillus niger* and *Aspergillus fumigatus,* varieties of Trichophyton, such as *Trichophton mentagrophytes,* varieties of Microsporon, such as *Microsporon felineum* and varieties of Penicillium, such as *Penicillium commune.* This list of micro-organisms in no way implies a limitation of the germs which can be combated but is only illustrative.

Examples which may be mentioned of fields of application in medicine are: dermatomycoses and systemic mycoses caused by *Trichophyton mentagrophytes* and other varieties of Trichophyton, varieties of microsporon, *Epidermophyton floccosum,* blastomyces and biphase fungi as well as moulds.

As stated above, the invention also relates to the use in medicine of the compounds of the invention.

The present invention provides a pharmaceutical composition containing as active ingredient a compound of the invention in admixture with a solid or liquefied gaseous diluent, or in admixture with a liquid diluent other than a solvent of a molecular weight less than 200 (preferably less than 350) except in the presence of a surface active agent.

The invention further provides a pharmaceutical composition containing as active ingredient a compound of the invention in the form of a sterile and/or physiologically isotonic aqueous solution.

The invention also provides a medicament in dosage unit form comprising a compound of the invention.

The invention also provides a medicament in the form of tablets (including lozenges and granules), dragees, capsules, pills, ampoules or suppositories comprising a compound of the invention.

"Medicament" as used in this Specification means physically discrete coherent portions suitable for medical administration. "Medicament in dosage unit form" as used in this Specification means physically discrete coherent units suitable for medical administration each containing a daily dose or a multiple (up to four times) or submultiple (down to a fortieth) of a daily dose of the compound of the invention in association with a carrier and/or enclosed within an envelope. Whether the medicament contains a daily dose or, for example, a half, a third or a quarter of a daily dose will depend on whether the medicament is to be administered once or, for example, twice, three times or four times a day respectively.

The pharmaceutical compositions according to the invention may, for example, take the form of ointments, gels, pastes, creams, sprays (including aerosols), lotions, suspensions, solutions and emulsions of the active ingredient in aqueous or non-aqueous diluents, syrups, granulates or powders.

The diluents to be used in pharmaceutical compositions (e.g. granulates) adapted to be formed into tablets, dragees, capsules and pills include the following: (a) fillers and extenders, e.g. starch, sugars, mannitol, and silicic acid; (b) binding agents, e.g. carboxymethyl cellulose and other cellulose derivatives, alginates, gelatine and polyvinyl pyrrolidone; (c) moisturizing agents, e.g. glycerol; (d) disintegrating agents, e.g. agar-agar, calcium carbonate and sodium bicarbonate; (e) agents for retarding dissolution e.g. paraffin; (f) resorption accelerators, e.g. quaternary ammonium compounds; (g) surface active agents, e.g. cetyl alcohol, glycerol monostearate; (h) adsorptive carriers, e.g. kaolin and bentonite; (i) lubricants, e.g. talc, calcium and magnesium stearate and solid polyethyl glycols.

The tablets, dragees, capsules and pills formed from the pharmaceutical compositions of the invention can have the customary coatings, envelopes and protective matrices, which may contain opacifiers. They can be so constituted that they release the active ingredient only or preferably in a particular part of the intestinal tract, possibly over a period of time. The coatings, envelopes and protective matrices may be made, for example, of polymeric substances or waxes.

The ingredient can also be made up in microencapsulated form together with one or several of the above-mentioned diluents.

The diluents to be used in pharmaceutical compositions adapted to be formed into suppositories can, for example, be the usual water-soluble diluents, such as polyethylene glycols and fats (e.g. cocoa oil and high esters [e.g. $C_{14}$-alcohol with $C_{16}$-fatty acid]) or mixtures of these diluents.

The pharmaceutical compositions which are ointments, pastes, creams and gels can, for example, contain the usual diluents, e.g. animal and vegetable fats, waxes, paraffins, starch, tragacanth, cellulose derivatives, polyethylene glycols, silicones, bentonites, silicic acid, talc and zinc oxide or mixtures of these substances.

The pharmaceutical compositions which are powders and sprays can, for example, contain the usual diluents, e.g. lactose, talc, silicic acid, aluminium hydroxide, calcium silicate, and polyamide powder or mixtures of these substances. Aerosol sprays can, for example, contain the usual propellants, e.g. chlorofluorohyrocarbons.

The pharmaceutical compositions which are solutions and emulsions can, for example, contain the customary diluents (with, of course, the above-metnioned exclusion of solvents having a molecular weight below 200 except in the presence of a surface-active agent), such as solvents, dissolving agents and emulsifiers; specific examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide, oils [for example ground nut oil], glycerol, tetrahydrofurfuryl alcohol, polyethylene glycols and fatty acid esters of sorbitol or mixtures thereof.

For parenteral administration, solutions and emulsions should be sterile, and, if appropriate, blood-isotonic.

The pharmaceutical compositions which are suspensions can contain the usual diluents, such as liquid diluents, e.g. water, ethyl alcohol, propylene glycol, surface-active agents (e.g. ethoxylated isostearyl alcohols, polyoxyethylene sorbite and sorbitane esters), microcrystalline cellulose, aluminium metahydroxide, bentonite, agar-agar and tragacanth or mixtures thereof.

All the pharmaceutical compositions according to the invention can also contain colouring agents and preservatives as well as perfumes and flavouring additions (e.g. peppermint oil and eucalyptus oil) and sweetening agents (e.g. saccharin).

The pharmaceutical compositions according to the invention generally contain from 0.1 to 99.5%, usually from 0.5 to 95% of the active ingredient by weight of the total composition.

In addition to a compound of the invention, the pharmaceutical compositions and medicaments according to the invention can also contain other pharmaceutically active compounds. They may also contain a plurality of compounds of the invention.

Any diluent in the medicaments of the present invention may be any of those mentioned above in relation to the pharmaceutical compositions of the present invention. Such medicaments may include solvents of molecular weight less than 200 as sole diluent.

The discrete coherent portions constituting the medicament according to the invention will generally be adapted by virtue of their shape or packaging for medical administration and may be, for example, any of the following: tablets (including lozenges and granulates), pills, dragees, capsules, suppositories and ampoules. Some of these forms may be made up for delayed release of the active ingredient. Some, such as capsules, include a protective envelope which renders the portions of the medicament physically discrete and coherent.

The preferred daily dose for administration of the medicaments of the invention is 2.5 g to 10 g of active ingredient.

The product of the above-mentioned pharmaceutical compositions and medicaments is carried out by any method known in the art, for example, by mixing the active ingredient(s) with the diluent(s) to form a pharmaceutical composition (e.g. a granulate) and then forming the composition into the medicament (e.g. tablets).

This invention further provides a method of combating (including prevention, relief and cure of) the above-mentioned diseases in warm-blooded animals, which comprises administering to the animals a compound of the invention alone or in admixture with a diluent or in the form of a medicament according to the invention.

It is envisaged that these active compounds will be administered perorally, parenterally (for example intramuscularly, intraperitoneally, subcutaneously and intravenously), rectally or locally, preferably parenterally, especially intravenously. Preferred pharmaceutical compositions and medicaments are therefore those adapted for administration such as parenteral administration. Administration in the method of the invention is preferably parenteral administration.

In general it has proved advantageous to administer amounts of from 10 mg to 300 mg/kg, preferably 50 to 200 mg/kg, of body weight per day to achieve effective results. Nevertheless, it can at times be necessary to deviate from those dosage rates, and in particular to do so as a function of the nature and body weight of the human or animal subject to be treated, the individual reaction of this subject to the treatment, the type of formulation in which the active ingredient is administered and the mode in which the administration is carried out, and the point in the progress of the disease or interval at which it is to be administered. Thus it may in some case suffice to use less than the above-mentioned minimum dosage rate, whilst other cases the upper limit mentioned must be exceeded to achieve the desired results. Where larger amounts are administered it can be advisable to divide these into several individual administrations over the course of the day.

The following Examples A and B illustrate the antimicrobial activity of the compounds used in the invention.

EXAMPLE A

Antimycotis in vitro activity

Description of the experiment:

In vitro tests were carried out in a series dilution test with germ inocula of an average of $5 \times 10^4$ germs/ml of substrate. The nutrient medium was (a) for dermatophytes and moulds: Sabouraud's milieu d'epreuve and (b) for yeasts: meat extract/glucose broth.

The incubation temperature was 20° C. and the duration of incubation was 24 to 96 hours.

In these experiments, the compounds according to the invention exhibited good minimum inhibitory concentrations against the above-mentioned fungi.

EXAMPLE B

Antimicrobial in vivo activity (oral) in candidosis of mice

Description of the experiment:

Mice of the SPF-CF$_1$ type were infected intravenously with $1-2 \times 10^6$ logarithmically growing Candida cells, which were suspended in physiological sodium chloride solution. The animals were treated orally one hour before and seven hours after the infection, with, in each case, 50–100 mg/kg of body weight of the formulations.

Result:

Untreated animals died 3 to 6 days after infection. The survival rate on the 6th. day after infection was about 5% in the case of untreated control animals.

1-[2,4-Dichloro-β-(2,4-dichlorobenzyloxy)-phenylethyl]-imidazole nitrate ("Miconazol" (Trade Mark)), which is known, exhibited no action at this dosage.

In contrast, the compounds according to the invention exhibited a good to very good action.

The following Examples illustrate the preparation of compounds of the invention.

EXAMPLE 1

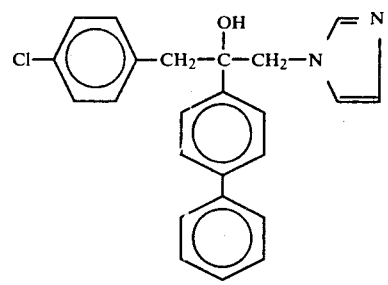

(Process variant a)

A solution of 13.1 g (0.05 mol) of 4-biphenylyl imidazol-1-yl-methyl ketone in 500 ml of benzene is added dropwise to a 4-chlorobenzyl-magnesium chloride solution, obtained from 6.1 g (0.25 mol) of magnesium and 40.2 g (0.25 mol) of 4-chlorobenzyl chloride in 150 ml of ether. Thereafter, the ether is distilled off and the reaction mixture is heated to 80° C. for about 8 hours. The cooled solution is poured onto an ammonium chloride solution and the organic phase is separated off, washed with water and dried over sodium sulphate. After distilling off the benzene, the crystal sludge which remains is stirred with ether and the crystals are filtered off and recrystallised from acetonitrile. 3.5 g (18% of theory) of 2-(4-biphenylyl)-1-(4-chlorophenyl)-3-(imidazol-1-yl)-propan-2-ol of melting point 182° C. are obtained.

Preparation of the starting material

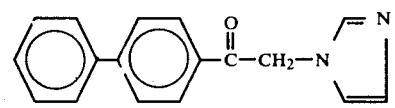

39 g (0.14 mol) of 4-phenylphenacyl bromide are introduced in portions into a solution of 48.2 g (0.7 mol) of imidazole in 140 ml of dimethylformamide, whilst cooling. The mixture is allowed to subsequently react for 15 hours and the solution is poured into water. The crystal mass which has separated out is recrystallised from ethanol. 24 g (65% of theory) of 4-biphenylyl imidazol-1-yl-methyl ketone of melting point 198° C. are obtained.

EXAMPLE 2

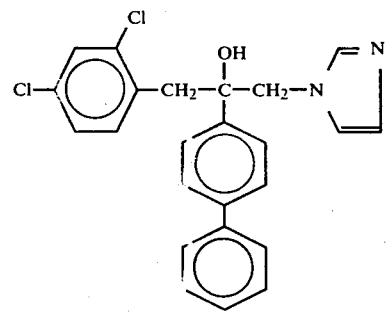

(Process variant b)

A solution of 39.15 g (0.1 mol) of 2-(4-biphenylyl)-3-chloro-1-(2,4-dichlorophenyl)-propan-2-ol in 300 ml of acetonitrile is added dropwise to a suspension of 3.6 g (0.12 mol) of sodium hydride and 8.2 g (0.12 mol) of imidazole in 200 ml of acetonitrile. After heating to 80° C. for 3 hours, the cooled reaction mixture is filtered and the crystal mass is washed with water and with acetonitrile. 32.5 g (77% of theory) of 2-(4-biphenylyl)-1-(2,4-dichlorophenyl)-3-(imidazol-1-yl)-propan-2-ol of melting point 168° C. are obtained.

Preparation of the starting material

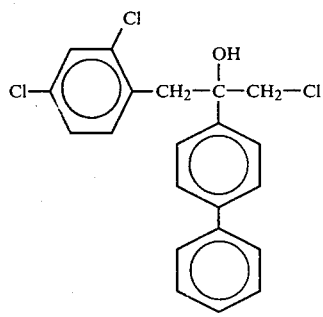

69.3 g (0.3 mol) of 4-phenylphenacyl chloride are added in portions to a solution of 0.6 mol of 2,4-dichlorobenzyl-magnesium chloride, obtained from 15.9 g (0.65 mol) of magnesium and 117.3 g (0.6 mol) of 2,4-dichlorobenzyl chloride in 300 ml of ether. The reaction mixture is then poured onto aqueous ammonium chloride solution and the ether phase is separated off, washed with water, dried over sodium sulphate and evaporated. The oil which remains is extracted with petroleum ether and the petroleum ether solution is evaporated. The crystals are filtered off and dried. 62 g (53% of theory) of 2-(4-biphenylyl)-3-chloro-1-(2,4-dichlorophenyl)-propan-2-ol of melting point 84° C. are obtained.

EXAMPLE 3

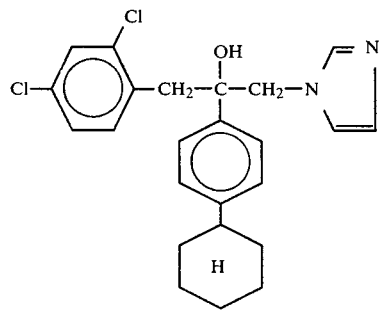

(Process variant b)

A solution of 39.8 g (0.1 mol) of 2-(4-cyclohexylphenyl)-3-chloro-1-(2,4-dichlorophenyl)-propan-2-ol in 200 ml of acetonitrile is added dropwise to a suspension of 3.6 g (0.12 mol) of sodium hydride and 8.2 g (0.12 mol) of imidazole in 200 ml of acetonitrile. After heating the mixture to 80° C. for three hours, it is filtered and the crystal mass is washed with water and recrystallised from acetonitrile. 24.9 g (58% of theory) of 2-(4-cyclohexylphenyl)-1-(2,4-dichlorophenyl)-3-(imidazol-1-yl)-propan-2-ol of melting point 142° C. are obtained.

Preparation of the starting material

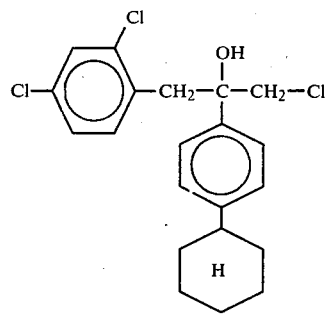

A solution of 47.3 g (0.2 mol) of 4-cyclohexylphenacyl chloride in 200 ml of ether is added dropwise to a solution of 0.4 mol of 2,4-dichlorobenzyl magnesium chloride, obtained from 10.6 g (0.44 mol) of magnesium and 78 g (0.4 mol) of 2,4-dichlorobenzyl chloride in 150 ml of ether. The reaction mixture is poured onto aqueous ammonium chloride solution and the ether phase is separated off, washed with water, dried over sodium sulphate and evaporated. 79.5 g (99% of theory) of 2-(4-cyclohexyl)-3-chloro-1-(2,4-dichlorophenyl)-propan-2-ol of refractive index $n_D^{20} = 1.5780$ are obtained.

The compounds in Table 1 below are obtained in a corresponding manner, either by process variant (a) or by process variant (b):

TABLE 1

$$R-CH_2-\underset{\underset{\displaystyle \text{Ar}}{|}}{\overset{\overset{\displaystyle OH}{|}}{C}}-CH_2-N\diagup\!\!\!\diagdown\text{N}$$

where Ar bears substituents $R^1$, $R^2$, $R_n^3$.

| Ex. No. | R | $R^1$ | $R^2$ | $R_n^3$ | Melting point (°C.) |
|---|---|---|---|---|---|
| 4 | -C₆H₄-Cl | 4-C₆H₄-Cl | H | — | 142 |
| 5 | -C₆H₅ | 4-C₆H₅ | H | — | 219 |
| 6 | 3-F-C₆H₄- with 4-Cl | 4-C₆H₅ | H | — | 180 |
| 7 | 3-Cl-C₆H₄- with 4-Cl | 4-C₆H₅ | H | — | 197 |
| 8 | 3-Cl-C₆H₄- | 4-C₆H₅ | H | — | 190 |
| 9 | -C₆H₃(Cl)(Cl) | 4-C₆H₅ | H | — | 134 |
| 10 | -C₆H₄-Cl | 3,4-(CH₂)₃— | | — | 135 |

TABLE 1-continued

Structure: R—CH₂—C(OH)(CH₂—N(imidazole))—phenyl with $R_n^3$, $R^2$, $R^1$ substituents

| Ex. No. | R | R¹ | R² | $R_n^3$ | Melting point (°C.) |
|---|---|---|---|---|---|
| 11 | 4-Cl-C₆H₄ | 4-H-C₆H₄ | H | — | 186 |
| 12 | 4-Cl-C₆H₄ | 3,4-(CH₂)₄ | | — | 130 |
| 13 | C₆H₅ | 4-Cl-C₆H₄ | H | — | 230 |
| 14 | 4-F-C₆H₄ | 4-C₆H₅ | H | — | 186 |
| 15 | 2-Cl-C₆H₄ | 4-Cl-C₆H₄ | H | — | 198 |
| 16 | 4-F-C₆H₄ | 4-Cl-C₆H₄ | H | — | 196 |
| 17 | 2-Cl-C₆H₄ (with Cl) | 4-Cl-C₆H₄ | H | — | 186 |
| 18 | 4-Cl-C₆H₄ | 4-Cl-C₆H₄ (2-Cl) | H | — | 146 |
| 19 | C₆H₅ | 4-Cl-C₆H₄ (2-Cl) | H | — | 167 |
| 20 | 4-Cl-C₆H₄ | 4-Cl-C₆H₄ (2-Cl) | H | — | 206 |
| 21 | 4-F-C₆H₄ | 4-Cl-C₆H₄ (2-Cl) | H | — | 152 |
| 22 | 4-F-C₆H₄ | 4-Cl-C₆H₄ (2-Cl) | H | — | 200 |
| 23 | 2,3-Cl₂-C₆H₃ | 2-Cl-C₆H₄ | H | — | 132 |
| 24 | 2,4-Cl₂-C₆H₃ | 2-Cl-C₆H₄ | H | — | 130 |
| 25 | 2-Cl-C₆H₄ | 2-Cl-C₆H₄ | H | — | 110 |
| 26 | 2,4-Cl₂-C₆H₃ | 4-C₆H₅ | H | — | 225(xHCl) |
| 27 | 4-Cl-C₆H₄ | 4-Cl-C₆H₄ | H | — | 180(xHCl) |
| 28 | 4-Cl-C₆H₄ | 4-Cl-C₆H₄ | H | — | 215(xH₂SO₄) |
| 29 | 4-Cl-C₆H₄ | 4-Cl-C₆H₄ | H | — | 155(xHNO₃) |
| 30 | 4-Cl-C₆H₄ | 4-Cl-C₆H₄ | H | — | 136 (xCH₃COCH) |
| 31 | 4-Cl-C₆H₄ | 4-Cl-C₆H₄ | H | — | 260(xH₃PO₄) |
| 32 | 2,3-Cl₂-C₆H₃ | 4-Cl-C₆H₄ | H | — | 206 |
| 33 | 2,3-Cl₂-C₆H₃ | 4-Cl-C₆H₄ | H | — | 110 |
| 34 | 2,3-Cl₂-C₆H₃ | 4-Cl-C₆H₄ | H | — | 210 |
| 35 | 2,3-Cl₂-C₆H₃ | 4-Cl-C₆H₄ | H | — | 150 |

Among the new hydroxypropyl-imidazole salts of the invention, those salts that are pharmaceutically acceptable are particularly important and are preferred.

The new free hydroxypropyl-imidazoles of the general formula I and their salts can be interconverted in any suitable manner; methods for such interconversion are known in the art.

The present invention also comprises pharmaceutically acceptable bioprecursors of the active compounds of the present invention.

For the purposes of this specification the term 'pharmaceutically acceptable bioprecursor' of an active compound of the invention means a compound having a structural formula different from the active compound but which nonetheless, upon administration to a warm-blooded animal is converted in the patient's body to the active compound.

We claim:

1. A compound of the formula

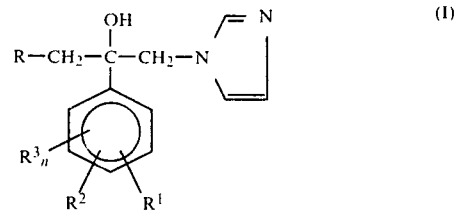

(I)

or a salt thereof in which
R denotes a phenyl, naphthyl or 1,2,3,4-tetrahydronaphthyl radical which is unsubstituted or substituted by halogen, $C_1$-$C_4$-alkyl, $C_1$-$C_4$-alkoxy, $C_1$-$C_4$-halogenoalkyl with up to 5 halogen atoms, $R^1$ denotes a phenyl or $C_3$-$C_7$-cycloalkyl radical which is unsubstituted or substituted by halogen, $C_1$-$C_4$-alkyl or $C_2$-$C_4$-alkenyl and $R^2$ denotes a hydrogen atom, or $R^1$ and $R^2$ together, in the o-position relative to one another, denote a methylene bridge having 3 to 5 methylene groups which is unsubstituted or substituted by halogen or $C_1$-$C_4$-alkyl or, together with the phenyl ring, denote a naphthyl radical, $R^3$ denotes a halogen atom or an $C_1$-$C_4$ alkyl, $C_1$-$C_4$ alkoxy or a $C_1$-$C_4$-halogenoalkyl group having up to 5 halogen atoms and n is 0,1,2 or 3.

2. A compound according to claim 1, in which R denotes a phenyl radical which is optionally monosubstituted or di-substituted by chlorine, fluorine or methyl, or a naphthyl or 1,2,3,4-tetrahydronaphthyl radical, $R^1$ denotes a phenyl, cyclopentyl or cyclohexyl radical which is optionally monosubstituted or disubstituted by chlorine, bromine, fluorine or methyl and $R^2$ denotes a hydrogen atom, or $R^1$ and $R^2$ together, in the ortho-position relative to each other, denote a trimethylene, tetramethylene or pentamethylene bridge which is optionally substituted by chlorine or methyl, or, together with the phenyl ring, denote a naphthyl radical, $R_3$ denotes a chlorine or fluorine atom or a methyl group and n is 0 or 1.

3. An antimycotic pharmaceutical composition containing as an active ingredient an antimycotically effective amount of a compound according to claim 1 in admixture with a solid or liquefied gaseous diluent or in admixture with a liquid diluent other than a solvent of a molecular weight less than 200 except in the presence of a surface-active agent.

4. A pharmaceutical composition according to claim 3 in the form of a sterile or physiologically isotonic aqueous solution.

5. A composition according to claim 3 or 4 containing from 0.5 to 95% by weight of the said active ingredient.

6. A medicament in dosage unit form comprising an antimycotically effective amount of a compound according to claim 1 together with an inert pharmaceutical carrier.

7. A medicament of claim 6 in the form of tablets, pills, dragees, capsules, ampoules, or suppositories.

8. A method of combating mycoses in warm-blooded animals which comprises administering to the said animals an antimycotically effective amount of active compound according to claim 1 either alone or in admixture with a diluent or in the form of a medicament.

9. A method according to claim 8 in which the active compound is administered in an amount of 10 to 300 mg per kg body weight per day.

10. A method according to claim 9 in which the active compound is administered in an amount of 50 to 200 mg per kg body weight per day.

11. A method according to claim 9 or 10 in which the active compound is administered parenterally.

* * * * *